(12) United States Patent
Baik et al.

(10) Patent No.: US 6,943,257 B2
(45) Date of Patent: Sep. 13, 2005

(54) PROCESS FOR PREPARATION OF AROMATIC HALIDES FROM AROMATIC AMINES

(76) Inventors: Woon Phil Baik, 10 Myongji Village,San 33-1 Nam-Dong, Yongin-city, Kyunggi-do, 449-030 (KR); Jung Min Kim, 516-1308 Zoogong Apt, Chungkye 1-dong, Nowon-gu, Seoul, 139-221 (KR); Young Sam Kim, 555-24 Shinwol 6-dong, Yangchon-gu, Seoul, 158-096 (KR); Cheol Hun Yoon, 1212 Donga Apt, Chun-ri, Idong-myun, Youngin-city, Kyunggi-do, 449-830 (KR); Shin Jong Kim, 15/3, 272-4 Heugseok 2-dong, Dungjak-gu, Seoul, 156-072 (KR); Seok Woo Lee, 103-1203 Samsung raemian Apt, Naeson-dong, Uiwang-city, Kyunggi-do, 437-080 (KR)

( * ) Notice: Subject to any disclaimer, the term of this patent is extended or adjusted under 35 U.S.C. 154(b) by 277 days.

(21) Appl. No.: 10/276,309
(22) PCT Filed: Sep. 21, 2001
(86) PCT No.: PCT/KR01/01586
§ 371 (c)(1),
(2), (4) Date: Nov. 25, 2002
(87) PCT Pub. No.: WO02/053545
PCT Pub. Date: Jul. 11, 2002

(65) Prior Publication Data
US 2004/0092728 A1 May 13, 2004

(30) Foreign Application Priority Data
Dec. 28, 2000 (KR) .................................. 2000/0084187

(51) Int. Cl.$^7$ .................. C07D 211/72; C07D 211/84; C07D 213/72
(52) U.S. Cl. .................. 546/304; 546/345; 552/263; 562/493; 570/127; 570/182; 570/183; 568/315; 568/323; 568/332; 568/338; 568/705; 568/929; 568/933; 568/938
(58) Field of Search .................. 568/315, 323, 568/332, 338, 705, 929, 933, 938; 562/493; 570/127, 182, 183; 552/203; 546/304, 345

(56) References Cited

PUBLICATIONS

Smith et al., Notes "Application of the Isoamyl Nitrite–Diiodomethane Route to Aryl Iodides", J. Org. Chem., 1990, vol. 55, No. 8, pp. 2543–2545.

Majetich et al., "Electrophilic Aromatic Bromination Using Bromodimethylsulfonium Bromide Generated in Situ", J. Org. Chem., 1997, vol. 62, No. 13, pp. 4321–4326.

Braendlin et al., "Halegenation" in "Friedel–Crafts and Related Reactions", Ed. Olah. G., Interscience Publisher, NY, 1964, vol. III, part 2, p. 1517.

Wulfman, "The Chemistry of Diazonium and Diazo Groups", Ed. Patai, S., J. Wiley, NY, 1978, part 1, pp. 288–290.

Org. Syn. Coll., vol. 3, 1955, pp. 185–187.

Primary Examiner—Cecilia J. Tsang
Assistant Examiner—Raymond Covington
(74) Attorney, Agent, or Firm—Greenblum & Bernstein, P.LC.

(57) ABSTRACT

The present invention provides a process for preparing an aromatic bromide or aromatic iodide from an aromatic amine derivative using nitrite anion and halodimethylsulfonium halide generated in situ from hydrobromic acid/DMSO or hydriodic acid/DMSO. The process for producing compounds of the formula (1) is disclosed (1) wherein X is bromine or iodine: Y is carbon or nitrogen; $R^1$, $R^2$, $R^3$, $R^4$ and $R^5$ which may be the same or different and are selected independently from the group consisting of a hydrogen, a hologen, a $C_1$–$C_8$ alkyl, a $C_1$–$C_{10}$ alkoxy, a nitro, a formyl, an aryl, a benzyl, a $C_2$–$C_{10}$ alkylcarbonyl and an arylcarbonyl, provided that adjacent groups as selected from $R^1$, $R^2$, $R^3$, $R^4$ and $R^5$ may combine to form a ring.

13 Claims, No Drawings

PROCESS FOR PREPARATION OF AROMATIC HALIDES FROM AROMATIC AMINES

TECHNICAL FIELD

The present invention relates to a one-pot process for preparing aromatic halides from the corresponding aromatic amines using nitrite ions and halodimethylsulfoflium halides prepared in situ. In particular, the present invention is related to a process for preparing aromatic bromides or aromatic iodides by reacting the corresponding aromatic amines with nitrite ions and halodimethylsulfonium halides prepared in situ from dimethylsulfoxide (DMSO) and halohydric acid.

BACKGROUND ART

Aromatic bromides and iodides are versatile reagents that can be converted to a wide variety of materials. For over 50 years, substitution reactions of aromatic halides have been used in organic synthesis. These reactions give compounds containing new carbon-carbon or carbon-heteroatom bonds in high yields. Furthermore, a series of reactions that are characteristic for aromatic iodides alone has been discovered.

Several methods for preparing various classes of aromatic halides have been published in monographs, journal reviews and patents. Representative processes for preparing aromatic halides are: direct aromatic halogenation in which a hydrogen atom is substituted by a halogen atom using bromine or iodine [Braendlin, H. P. and McBee, E. T., "Friedel-Crafts and Related Reactions", Ed. Olah, G., Interscience Publisher, NY, 1964, Vol. 111, part 2, p 1517]; and the Sandmeyer reaction in which an amino group is substituted by a halogen atom via diazonium salt ["The Chemistry of Diazonium and Diazo Groups", Ed. Patai, S., J. Wiley, NY. 1978, part 1, p 288].

One drawback to direct aromatic halogenation has been the formation of other isomers as impurities. Direct iodination with $I_2$ is also possible using a mixture of nitric acid and sulfuric acid. However, the use of strong acids is extremely undesirable to the highly substituted arenes and heterocyclic compounds.

Since aromatic amines are generally more economical, most methods for preparing highly substituted aromatic halides have centered on improving the Sandmeyer reaction. The Sandmeyer reaction involves a 2-step process of diazotization followed by halogenation. First, the amino group is converted to diazonium salt by reacting it with nitrite ions under acidic conditions, and the nucleophilic halide ion is then substituted at the same position. The typical Sandmeyer reaction may be carried out in the presence of copper halide as a nucleophile (Org. Syn. Coll. Vol. 3, 1955, 185). However, the discharge of excess copper salt may cause environmental pollution. In addition, since the stability of diazonium salt is the most important factor in the Sandmeyer reaction, special conditions such as a low reaction temperature and filtration are required in the process.

Considering the wide application of aromatic halides, it is required that the innovation of a synthetic process of the aromatic halides in a low cost and simple while minimizing waste byproducts. Some modified Sandmeyer reactions that involve diazonium salt have been developed to achieve simplicity and low cost. Unlike methods that require sodium nitrite and acidic conditions to prepare diazonium salt, isoamyl nitrite is a useful and mild in situ diazotizing agent for the preparation of aromatic iodides (Smith, W. B., Ho, O. C., *J. Org. Chem.*, 1990, 55, 2543). Although the prior art is especially attractive when aromatic amines bear acid-labile groups and/or the reaction requires neutral conditions, it can be difficult to separate the product from excess diiodomethane.

In order to achieve the low cost of manufacturing and the decrease of environmental problems, the following factors should be considered:

(1) to develop diazotization for a one step reaction in situ; and (2) to develop an active nucleophile which can replace $CuBr$, $I_2$ or $CH_2I_2$.

DISCLOSURE OF INVENTION

Therefore, it is an object of the present invention to provide a novel process for directly producing aromatic halides by the use of an activated halide nucleophile.

Another object of the present invention is to provide aromatic halides which bear a halogen atom in any position of the benzene ring optionally.

Another object of the present invention is also to provide a process for directly producing aromatic halides while minimizing environmental pollution.

The present invention relates to a process for directly producing aromatic halides by reacting a corresponding aromatic amine and a nitrite ion with a halodimethylsulfonium halide prepared in situ from $DMSO(CH_3S(=O)CH_3)$ and a halohydric acid.

In the present invention, an aromatic amine is spontaneously converted to an aromatic halide via the in situ formation of a diazonium salt at room temperature. An aromatic amine is spontaneously transferred to diazonium salt by the addition of nitrite salt and halohydric acid in DMSO. Meanwhile, an activated halide nucleophile, halodimethylsulfonium halide, is simultaneously prepared in situ from the same halohydric acid and DMSO. Thus, the transformation of an amine group to a halogen group occurs in one step via diazotization-displacement using $NO_2^-/HX/DMSO$ at room temperature. The most important factor in this process is the use of halodimethylsulfonium halide as an activated nucleophilic agent prepared in situ.

BEST MODE FOR CARRYING OUT THE INVENTION

The present invention is directed to a novel process for producing compounds of the formula (1):

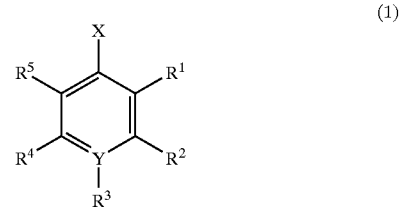

(1)

wherein
  X is bromine or iodine;
  Y is carbon or nitrogen;
  $R^1$, $R^2$, $R^3$, $R^4$ and $R^5$ which may be the same or different and are selected independently from the group consisting of a hydrogen, a halogen, a $C_1$–$C_8$ alkyl, a $C_1$–$C_{10}$ alkoxy, a nitro, a formyl, an aryl, a benzyl, a $C_2$–$C_{10}$ alkylcarbonyl and an arylcarbonyl, provided that adjacent groups as selected from among $R^1$, $R^2$, $R^3$, $R^4$ and $R^5$ may combine to form a ring.

The present invention is characterized by the use of halodimethylsulfonium halide as an activated nucleophilic agent for converting a diazonium salt to an aromatic halide. The halodimethylsulfonium halide is generated in situ (i.e., formed instantly in the reaction mixture) from halohydric acid and DMSO. The present invention has another advantage regarding the formation of diazonium salt, which is also prepared in situ from halohydric acid and nitrite ions in DMSO. Thus, the diazonium salt and halodimethylsulfonium halide are formed simultaneously in situ from the same halohydric acid by one-pot process.

In fact, bromodimethylsulfonium bromide has been used as a bromide nucleophile to substitute hydrogen atom(s) of an aromatic compound (Majetich, G., Hicks, R., Reister, S., *J. Org. Chem.* 1997, 62, 4321). As shown in chemical equation (1), when HBr is added while using DMSO as a solvent, bromodimethylsulfonium bromide is formed instantly, and substitution of a hydrogen atom of the benzene ring by bromide occurs simultaneously.

Eq. (1)

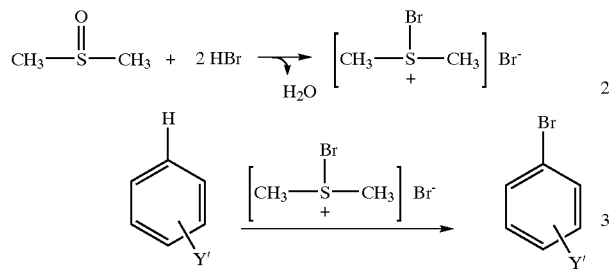

In this equation (1), Y' represents various substituents on the benzene ring.

The present invention is shown in equation (2):

Eq. (2)

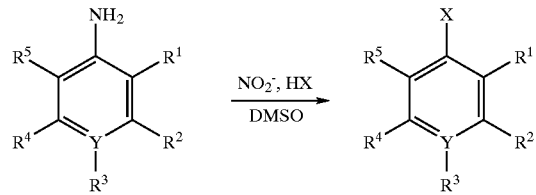

wherein X, Y, $R^1$ to $R^5$ are defined as above formula (1).

The present invention is carried out by dissolving $NO_2^-$ in DMSO, and then an aromatic amino compound (an aniline derivative or an amino pyridine derivative) and HBr (or HI) are added to the resulting mixture at room temperature. The order in which nitrite salt, hydrobromic acid (or hydriodic acid) and an aromatic amine are added is not critical to the reaction. In the reaction, the activated nucleophilic bromide (or iodide) of halodimethylsulfonium halide, which is formed at nearly the same time as the diazonium salt, directly attacks the diazonium salt to provide the aryl bromide compound (or aryl iodide) of the formula (1) shown in equation (2).

After confirming the compound of the formula (1) by thin layer chromatography, the product is obtained from the reaction mixture by extracting from an organic solvent such as ethyl ether. The product is isolated from the mixture by a standard work-up process such as evaporation and/or extraction, and then purified by a standard method such as recrystallization or column chromatography on silica gel.

In the present invention, a halohydric acid is used to prepare a halodimethylsulfonium halide and also acts as a strong acid in preparing diazonium salt. In the reaction, DMSO also plays two roles as a solvent dissolving nitrite salt and as a reactant involved in the preparation of nucleophilic halodimethylsulfonium halide. Since DMSO is a polar solvent, it also stabilizes the resultant diazonium salt.

Thus bromodimethylsulfonium bromide can be prepared by the reaction of HBr with DMSO as in equation (1). Similarly, iododimethylsulfonium iodide can be prepared by the reaction of HI and DMSO as in equation (3a). Also, bromodimethylsulfonium iodide (i.e. another type of iodide ion) can be prepared by the reactions of HBr with DMSO and by the replacement of bromide by iodide as in equation (3b).

Eq. (3a)

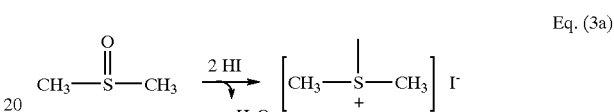

Eq. (3b)

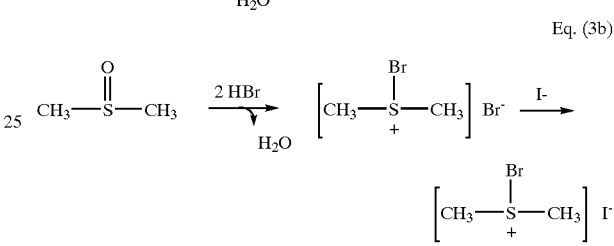

In the present invention, nitrite ion may be in any salt form in combination with sodium ion, potassium ion or ammonium ion.

The halohydric acid of the present invention may be either hydrobromic acid or hydriodic acid. Due to safety and handling considerations, aqueous halohydric acid or halohydric acid in glacial acetic acid solution are preferred. This is generally available as a commercial product containing about 30% to about 57% halohydric acid based on the solution of $H_2O$ or glacial acetic acid. Anhydrous halohydric acid may also be used. While the use of some water may be beneficial, it increases the reaction volume and thus decreases the batch efficiency.

The molar ratio of halohydric acid to aromatic amine should be about 2:1 to 6:1; preferably about 4:1. The molar ratio of nitrite to aromatic amine should be about 2:1 to 4:1. The use of less halohydric acid and nitrite may cause reduced product yields, while greater amounts should decrease the batch efficiency.

The third reactant, dimethylsulfoxide (DMSO), may be used in anhydrous form or in a mixture with another solvent, such as tetrahydrofuran, dimethylformamide, alcohol, or hexane.

The reaction is carried out at room temperature(25° C.) to 160° C., preferably from 35° C. to 80° C. At temperatures below about 25° C., the reaction may be too slow to be commercially feasible.

In the process, the reaction is generally complete within 30 minutes. If the conversion and selectivity of aromatic amines to halides have not been appreciably high, a catalytic amount of cuprous halide or cupric halide may also be used to promote the reaction. The molar ratio of cuprous halide (or cupric halide) to aromatic amine is preferably about 0.3:1.

The present invention can be applied to any kind of aromatic amine and also to polycyclic aromatic amines(I-a, I-b, I-c) or aminopyridine derivatives(I-d, I-e) as shown in below:

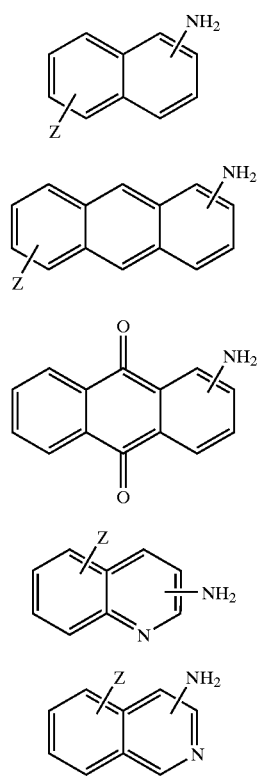

wherein Z represents a hydrogen, a halogen, a $C_1$–$C_8$ alkyl, a $C_1$–$C_{10}$ alkoxy, a nitro, a formyl, an aryl, a benzyl, a $C_2$–$C_{10}$ alkylcarbonyl or an arylcarbonyl.

The present invention offers several advantages: (1) the amino group in an aromatic amine compound can be transformed to bromine or iodine; (2) the process consists of just a one step; (3) the reaction time is short (eg., about 30 minutes), and the reaction temperature is mild (eg., room temperature); (4) the required equipment is inexpensive; and (5) the reaction can minimize environmental pollution.

Hereinafter, the present invention will be described in detail with reference to the preferred examples. The following examples are intended to further illustrate the process of the present invention and are not intended to limit the scope of the invention in any manner.

EXAMPLES 1–10

Use of Bromodimethylsulfonium Bromide Prepared by HBr and DMSO

Example 1

Synthesis of 4-bromobenzophenone

A solution of 48% aqueous HBr (2.31 ml, 20 mmol) dissolved in DMSO (25 ml) was added dropwise to a solution of 4-aminobenzophenone (0.986 g, 5 mmol) in a mixture of 25 ml of DMSO and $KNO_2$ (0.851 g, 10 mmol) at 35° C. with agitation. The added mixture was stirred at 35° C. for 10 minutes, and then transferred to a solution containing $K_2CO_3$ (5 g) in 100 ml ice-water. The reaction mixture was then taken up in ether, and then the ethereal extracts were washed with water and dried over anhydrous magnesium sulfate. Removal of the solvent under reduced pressure gave the crude 4-bromobenzophenone. The crude product was further purified by column chromatography to obtain 4-bromobenzophenone. The yield determined by gas chromatography was 72% (based on decane as an internal standard).

$^1$H-NMR (CDCl$_3$): δ 7.36 (t, 2H), 7.45 (t, 1H), 7.53 (d, 2H), 7.59 (d, 2H), 7.70 (d, 2H).

Example 2

Synthesis of 4'-bromoacetophenone

The same procedure as Example 1 was repeated except that 4-aminobenzophenone was substituted with 4'-aminoacetophenone (0.676 g, 5 mmol), to obtain 4'-bromoacetophenone. The yield determined by gas chromatography was 85% (based on decane as an internal standard).

$^1$H-NMR (CDCl$_3$):δ 2.55 (s, 3H), 7.54 (d, 2H), 7.75 (d, 2H).

Example 3

Synthesis of 1-bromo-5-chloro-2-nitrobenzene

The same procedure as Example 1 was repeated except that 4-aminobenzophenone was substituted with 5-chloro-2-nitroaniline (0.865 g, 5 mmol), to obtain 1-bromo-5-chloro-2-nitrobenzene. The yield determined by gas chromatography was 82% (based on decane as an internal standard).

$^1$H-NMR (CDCl$_3$): δ7.37 (d, 1H), 7.67 (s, 1H), 7.77 (d, 1H).

Example 4

Synthesis of 2-bromobiphenyl

The same procedure as Example 1 was repeated except that 4-aminobenzophenone was substituted with 4-aminobiphenyl with (0.846 g, 5 mmol), to obtain 2-bromobiphenyl. The yield determined by gas chromatography was 87% (based on decane as an internal standard).

$^1$H-NMR (CDCl$_3$): δ7.11 (t, 1H), 7.22 (t, 1H), 7.26 (t, 1H), 7.32 (t, 2H), 7.37 (d, 1H), 7.48 (d, 2H), 7.49 (d, 1H).

Example 5

Synthesis of 1-bromo-3,5-dinitrobenzene

The same procedure as Example 1 was repeated except that 4-aminobenzophenone was substituted with 3,5-dinitroaniline (0.916 g, 5 mmol), to obtain 1-bromo-3,5-dinitrobenzene. The yield determined by gas chromatography was 84% (based on decane as an internal standard).

$^1$H-NMR (CDCl$_3$):δ 8.72 (s, 2H), 9.00 (s, 1H).

Example 6

Synthesis of 1-bromo-2-methoxy-5-nitrobenzene

The same procedure as Example 1 was repeated except that 4-aminobenzophenone was substituted with 2-methoxy-5-nitroaniline (0.841 g, 5 mmol), to obtain 1-bromo-2-methoxy-5-nitrobenzene. The yield determined by gas chromatography was 78% (based on decane as an internal standard).

$^1$H-NMR (CDCl$_3$): δ3.94 (s, 3H), 6.90 (d, 1H), 8.13 (d, 1H), 8.36 (s, 1H).

Example 7

Synthesis of 4-bromobenzoic acid

The same procedure as Example 1 was repeated except that 4-aminobenzophenone was substituted with 4-aminobenzoic acid (0.686 g, 5 mmol), to obtain 4-bromobenzoic acid. The yield determined by gas chromatography was 70% (based on decane as an internal standard).

$^1$H-NMR (CDCl$_3$): δ7.64 (d, 2H), 7.89 (d, 2H).

Example 8

Synthesis of 1-bromonaphthalene

The same procedure as Example 1 was repeated except that 4-aminobenzophenone was substituted with 1-aminonaphthalene (0.716 g, 5 mmol), to obtain 1-bromonaphthalene. The yield determined by gas chromatography was 78% (based on decane as an internal standard).

$^1$H-NMR (CDCl$_3$): δ7.23 (t, 1H), 7.43 (t, 1H), 7.51 (t, 1H), 7.70 (d, 2H), 7.72 (d, 1H), 8.18 (d, 1H).

Example 9

Synthesis of 2-bromoanthraquinone

The same procedure as Example 1 was repeated except that 4-aminobenzophenone was substituted with 2-aminoanthraquinone (1.12 g, 5 mmol), to obtain 2-bromoanthraquinone. The yield determined by gas chromatography was 64% (based on decane as an internal standard).

$^1$H-NMR (CDCl$_3$): δ7.55 (t, 2H), 7.68 (d, 1H), 7.72 (d, 1H), 7.80 (d, 2H), 7.96 (s, 1H).

Example 10

Synthesis of 2-bromo-3-nitropyridine

The same procedure as example 1 was repeated except that 4-aminobenzophenone was substituted with 2-amino-3-nitropyridine (0.696 g, 5 mmol), to obtain 2-bromo-3-nitropyridine. The yield determined by gas chromatography was 72% (based on decane as an internal standard).

$^1$H-NMR (CDCl$_3$):δ 7.83 (t, 1H), 8.92 (d, 1H), 9.02 (d, 1H).

EXAMPLES 11–14

Use of Iododimethylsulfonium Iodide Prepared by HI and DMSO

Example 11

Synthesis of 4-iodobenzophenone

A solution of 57% aqueous HI (3.29 ml, 25 mmol) dissolved in DMSO (25 ml) was added dropwise to a solution of 4-aminobenzophenone (0.986 g, 5 mmol) in a mixture of 25 ml of DMSO and KNO$_2$ (0.851 g, 10 mmol) at 35° C. with agitation. The added mixture was stirred at 35° C. for 10 minutes and then was transferred to a solution containing K$_2$CO$_3$ (5 g) in 100 ml ice-water. The reaction mixture was then taken up in ether, and then the ethereal extracts were washed with water and dried over anhydrous magnesium sulfate. Removal of the solvent under reduced pressure gave the crude 4-iodobenzophenone. The crude product was further purified by column chromatography to obtain 4-iodobenzophenone. The yield determined by gas chromatography was 88% (based on decane as an internal standard).

1H-NMR (CDCl$_3$): δ7.36 (t, 2H), 7.45 (t, 1H), 7.47 (d, 2H), 7.70 (d, 2H), 7.74 (d, 2H).

Example 12

Synthesis of 1-iodo-2,4-difluorobenzene

The same procedure as Example 11 was repeated except that 4-aminobenzophenone was substituted with 2,4-difluoroaniline (0.646 g, 5 mmol) as the starting material. The yield determined by gas chromatography was 84% (based on decane as an internal standard).

1H-NMR (CDCl$_3$): δ6.51 (d, 1H), 6.44 (s, 1H), 7.60 (d, 1H).

Example 13

Synthesis of 1-iodo-2-methoxy-5-nitrobenzene

The same procedure as Example 11 was repeated except that 4-aminebenzophenone was substituted with 2-methoxy-5-nitroaniline (0.841 g, 5 mmol) as the starting material. The yield determined by gas chromatography was 93% (based on decane as an internal standard).

1H-NMR (CDCl$_3$): δ3.76 (s, 3H), 6.85 (d, 1H), 8.09 (d, 1H), 8.46 (s, 1H).

Example 14

Synthesis of 1-iodo-4-nitrobenzene

The same procedure as Example 11 was repeated except that 4-aminobenzophenone was substituted with 4-nitroaniline (0.691 g, 5 mmol) as the starting material. The yield determined by gas chromatography was 89% (based on decane as an internal standard).

1H-NMR (CDCl$_3$):δ 7.88 (d, 2H), 8.01 (d, 2H).

EXAMPLES 15–16

Use of Bromodimethylsulfonium Iodide Prepared by HBr, KI and DMSO

Example 15

Synthesis of 4-iodobenzophenone

A solution of 48% aqueous HBr (2.31 ml, 20 mmol) and KI (4.15 g, 25 mmol) dissolved in DMSO (25 ml) was added dropwise to a solution of 4-aminobenzophenone (0.986 g, 5 mmol) in a mixture of 25 ml of DMSO and KNO$_2$ (0.851 g, 10 mmol) at 35° C. with agitation. The mixture was stirred at 35° C. for 10 minutes, and then it transferred to a solution containing K$_2$CO$_3$ (5 g) in 100 ml ice-water. The reaction mixture was then taken up in ether, and the ethereal extracts were washed with water and dried over anhydrous magnesium sulfate. Removal of the solvent under reduced pressure gave the crude 4-iodobenzophenone. The crude product was further purified by column chromatography to obtain 4-iodobenzophenone. The yield determined by gas chromatography was 90% (based on decane as an internal standard).

1H-NMR (CDCl$_3$): δ7.36 (t, 2H), 7.45 (t, 1H), 7.47 (d, 2H), 7.70 (d, 2H), 7.74 (d, 2H).

Example 16

Synthesis of 2-iodoanthraquinone

The same procedure as Example 15 was repeated except that 4-aminobenzophenone was substituted with 2-aminoanthraquinone (1.12 g, 5 mmol), to obtain 2-iodoanthraquinone. The yield determined by gas chromatography was 90% (based on decane as an internal standard).

1H-NMR (CDCl$_3$):δ 7.55 (t, 2H), 7.57 (d, 1H), 7.80 (d, 2H), 7.93 (d, 1H), 8.18 (s, 1H).

Example 17

Synthesis of 1-iodonaphthalene

The same procedure as example 15 was repeated except that 4-aminobenzophenone was substituted with 1-aminonaphthalene (0.716 g, 5 mmol) as shown in Table 1, to obtain 1-iodonaphthalene. The yield determined by gas chromatography was 45% (based on decane as an internal standard).

1H-NMR (CDCl$_3$):δ 6.83 (t, 1H), 7.24 (t, 1H), 7.29 (t, 1H), 7.41 (d, 1H), 7.46 (d, 1H), 7.84 (d, 1H), 7.93 (d, 1H).

Example 18

Synthesis of 1-iodonaphthalene

The same procedure as Example 17 was repeated except that HBr and KI were substituted with 57% aqueous HI (25 mmol) as shown in Table 1, to obtain 1-iodonaphthalene. The yield determined by gas chromatography was 65% (based on decane as an internal standard).

1H-NMR (CDCl$_3$):δ 6.83 (t, 1H), 7.24 (t, 1H), 7.29 (t, 1H), 7.41 (d, 1H), 7.46 (d, 1H), 7.84 (d, 1H), 7.93 (d, 1H).

Example 19

Synthesis of 1-iodonaphthalene

The same procedure as example 18 was repeated except that CuI (1.5 mmol) was used as a catalyst as shown in Table 1, to obtain 1-iodonaphthalene. The yield determined by gas chromatography was 93% (based on decane as an internal standard).

1H-NMR (CDCl$_3$):δ 6.83 (t, 1H), 7.24 (t, 1H), 7.29 (t, 1H), 7.41 (d, 1H), 7.46 (d, 1H), 7.84 (d, 1H), 7.93 (d, 1H).

TABLE 1

| | Halodimethylsulfonium halide | | | | |
|---|---|---|---|---|---|
| Example | Iodide ion (mmol) | DMSO | CuI (mmol) | Reaction time (h) | Yield % |
| 17 | HBr (20), KI (25) | 25 ml | none | 2 | 45 |
| 18 | HI (25) | 25 ml | none | 3 | 65 |
| 19 | HI (25) | 25 ml | 1.5 | 0.5 | 93 |

Example 20

Synthesis of 2-iodo-3-nitropyridine

The same procedure as example 15 was repeated except that 4-aminobenzophenone was substituted with 2-amino-3-nitropyridine (0.696 g, 5 mmol) as shown in Table 2, to obtain 2-iodo-3-nitropyridine. The yield determined by gas chromatography was 40% (based on decane as an internal standard).

H-NMR (CDCl$_3$):δ 7.76 (t, 1H), 8.49 (d, 1H), 8.86 (d, 1H).

Example 21

Synthesis of 2-iodo-3-nitropyridine

The same procedure as Example 20 was repeated except that HBr and KI were substituted with 57% aqueous HI (25 mmol) as shown in Table 2, to obtain 2-iodo-3-nitropyridine. The yield determined by gas chromatography was 59% (based on decane as an internal standard).

H-NMR (CDCl$_3$):δ 7.76 (t, 1H), 8.49 (d, 1H), 8.86 (d, 1H).

Example 22

Synthesis of 2-iodo-3-nitropyridine

The same procedure as Comparative Example 21 was repeated except that CuI (1.5 mmol) was used as a catalyst as shown in Table 2, to obtain 2-iodo-3-nitropyridine. The yield determined by gas chromatography was 89% (based on decane as an internal standard).

H-NMR (CDCl$_3$):δ 7.76 (t, 1H), 8.49 (d, 1H), 8.86 (d, 1H).

TABLE 2

| | Halodimethylsulfonium halide | | | | |
|---|---|---|---|---|---|
| Example | Iodide ion (mmol) | DMSO | CuI (mmol) | Reaction time (h) | Yield % |
| 20 | HBr (20), KI (25) | 25 ml | None | 2 | 40 |
| 21 | HI (25) | 25 ml | None | 3 | 59 |
| 22 | HI (25) | 25 ml | 1.5 | 0.5 | 89 |

As previously described, according to the present invention, bromine or iodine substitution of any kind of aromatic amine compound can be performed by a one-pot reaction under mild conditions. The present invention particularly has an advantage of the position options of the halide in the aromatic compounds. The present invention can be simply performed while minimizing environmental pollution and without requiring the additional costs for special devices and treatment.

It will be apparent to those skilled in the art that various modifications and variations can be made to the process of this invention without departing from the spirit or scope of the invention. It is intended that these modifications and variations of this invention are to be included as part of the invention, provided that they come within the scope of the appended claims and their equivalents.

What is claimed is:

1. A process for producing aromatic halide of the formula (1) which comprises:

converting an aromatic amine compound to a corresponding aromatic halide in the presence of a halodimethylsulfonium halide as an active nucleophilic agent

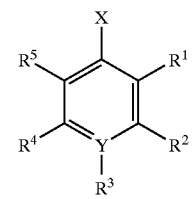

(1)

wherein

X is bromine or iodine;

Y is carbon or nitrogen;

$R^1$, $R^2$, $R^3$, $R^4$ and $R^5$ which may be the same or different and are selected independently from the group consisting of a hydrogen, a halogen, a $C_1$–$C_8$ alkyl, a $C_1$–$C_{10}$ alkoxy, a nitro, a formyl, an aryl, a benzyl, a $C_2$–$C_{10}$ alkylcarbonyl and an arylcarbonyl, provided that adjacent groups as selected from among $R^1$, $R^2$, $R^3$, $R^4$ and $R^5$ may combine to form a ring.

2. The process according to claim 1, wherein the converting is conducted by a one-pot process in which said aromatic amine compound is treated with a mixture of nitrite ion, dimethylsulfoxide and halohydric acid, diazonium salt is generated in situ, and said halohydric acid and dimethylsulfoxide simultaneously from said halodimethylsulfonium halide in situ at a temperature ranging from about 25° C. to about 160° C.

3. The process according to claim 2, wherein the temperature ranges from about 35° C. to about 80° C.

4. The process according to claim 2, wherein said halohydric acid is hydrobromic acid or hydriodic acid.

5. The process according to claim 4, wherein said halohydric acid is presented in an amount of 2 to 6 mol based on a mol of aromatic amine.

6. The process according to claim 5, wherein said halohydric acid is hydrobromic anhydride or about 30%~57% hydrobromic acid in aqueous solution or acetic acid solution.

7. The process according to claim 5, wherein said halohydric acid is hydriodic anhydride or about 30%~57% hydriodic acid in aqueous solution or acetic acid solution.

8. The process according to claim 2, wherein said nitrite ion is in a salt form combined with sodium, potassium or ammonium.

9. The process according to claim 8, wherein said nitrite ion is present in an amount of 2 to 4 mol based on a mol of aromatic amine.

10. The process according to claim 2, wherein said dimethylsulfoxide is an anhydrous form or in a mixture with a solvent selected from the group consisting of tetrahydrofuran, dimethylformamide, $C_1$–$C_4$ alcohol and hexane.

11. The process according to claim 2, wherein the aromatic amine is a compound selected from the group consisting of:

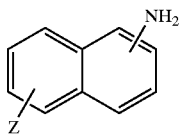
I-a

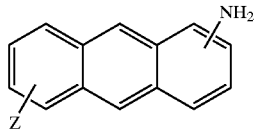
I-b

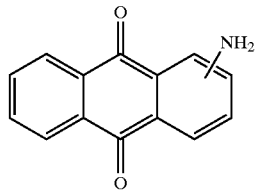
I-c

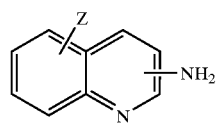
I-d

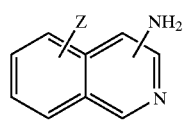
I-e wherein

Z represents a hydrogen, a halogen, a $C_1$–$C_8$ alkyl, a $C_1$–$C_{10}$ alkoxy, a nitro, a formyl, an aryl, a benzyl, a $C_2$–$C_{10}$alkylcarbonyl or an arylcarbonyl.

12. The process according to claim 11, wherein the converting is conducted in presence of a catalyst selected from cuprous halide or cupric halide.

13. The process according to claim 12, wherein an amount of said cuprous halide or cupric halide is about 0.3 mol based on a mol of aromatic amine.

* * * * *

UNITED STATES PATENT AND TRADEMARK OFFICE
CERTIFICATE OF CORRECTION

PATENT NO.       : 6,943,257 B2
APPLICATION NO.  : 10/276309
DATED            : September 13, 2005
INVENTOR(S)      : W.P. BAIK et al.

It is certified that error appears in the above-identified patent and that said Letters Patent is hereby corrected as shown below:

On the cover of the printed patent, at Item (57), Abstract, line 11, "hologen" should be ---halogen---.

Signed and Sealed this

Eighteenth Day of July, 2006

JON W. DUDAS
*Director of the United States Patent and Trademark Office*